United States Patent [19]

Isshiki et al.

[11] Patent Number: 4,659,865
[45] Date of Patent: Apr. 21, 1987

[54] PROCESS FOR PRODUCING ETHYLIDENEDIACETATE

[75] Inventors: Tomiya Isshiki, Tokyo; Yasuhiko Kijima; Yuh Miyauchi, both of Matsudo; Takayuki Yasunaga, Tokyo, all of Japan

[73] Assignee: Mitsubishi Gas Chemical Co., Inc., Tokyo, Japan

[21] Appl. No.: 636,067

[22] Filed: Jul. 30, 1984

Related U.S. Application Data

[63] Continuation of Ser. No. 429,156, Sep. 30, 1982, abandoned, which is a continuation of Ser. No. 185,685, Sep. 10, 1980, abandoned.

[30] Foreign Application Priority Data

Sep. 13, 1979 [JP] Japan ................. 59-117660

[51] Int. Cl.⁴ .............. C07C 67/36; C07C 67/38
[52] U.S. Cl. ................. 560/232; 560/240; 560/263
[58] Field of Search ............ 560/232, 240, 263

[56] References Cited

U.S. PATENT DOCUMENTS

| 2,789,137 | 4/1957 | Reppe et al. | 260/549 |
| 4,133,963 | 1/1979 | Holmes | 560/232 |
| 4,201,868 | 5/1980 | Slinkard | 560/232 |
| 4,221,918 | 9/1980 | Suzuki | 560/263 |
| 4,241,219 | 12/1980 | Wan | 560/232 |
| 4,323,697 | 4/1982 | Rizkalla | 560/232 |
| 4,336,399 | 6/1982 | Isshiki et al. | 560/61 |

FOREIGN PATENT DOCUMENTS

| 2016061 | 11/1970 | Fed. Rep. of Germany | 560/263 |
| 2404618 | 4/1979 | France | 560/61 |
| 3925031 | 11/1964 | Japan | 560/232 |
| 51-115409 | 10/1976 | Japan . | |
| 1538782 | 1/1979 | United Kingdom | 560/232 |

Primary Examiner—Werren B. Lone
Attorney, Agent, or Firm—Frishauf, Holtz, Goodman & Woodward

[57] ABSTRACT

A process for producing ethylidenediacetate which comprises reacting methyl acetate or dimethyl ether, carbon monoxide and hydrogen in the presence of catalyst comprising as a secondary-component at least one material selected from the group consisting of, iodides and bromides and as a main component combination of (1) at least one material selected from the group consisting of nickel and nickel compounds, at least one material selected from the group consisting of cobalt and cobalt compounds under substantially anhydrous conditions is disclosed. According to the present invention synthesis of ethylidenediacetate is achieved by using a cheaper catalyst than the prior catalyst.

18 Claims, No Drawings

PROCESS FOR PRODUCING ETHYLIDENEDIACETATE

This application is a continuation of application Ser. No. 429,156, filed Sept. 30, 1982, which, in turn, is a continuation of Ser. No. 185,685, filed Sept. 10, 1980, now abandoned.

BACKGROUND OF THE INVENTION

This invention relates to a process for producing ethylidenediacetate which comprises causing hydrocarbonylation reaction of methyl acetate or dimethyl ether with carbon monoxide and hydrogen.

In the prior art, ethylidenediacetate was synthesized from acetylene and acetic acid or by reacting acetaldehyde with acetic anhydride.

Recently, a process for producing ethylidenediacetate by reacting methyl acetate or dimethyl ether with carbon monoxide and hydrogen in the presence of a catalyst was proposed (refer to Japanese Patent Publication (laid open) No. 115409/1976). In the process disclosed in this Patent Publication, noble metals belonging to Group VIII of the Periodic Table and halides were essential components of the catalyst for hydrocarbonylation reaction. There is the passage "co-catalysts can be used together with the noble metal catalyst in order to enhance the reactivity" in the Patent Publication.

Furthermore, in Working Examples 1–29 of the Patent Publication, only rhodium or palladium was used as the main catalyst. However, in Working Examples 5 and 8, little ethylidenediacetate is formed in the absence of an organic or inorganic co-catalyst. In other words, the invention of Patent Publication No. 115409/1976 relates to a process for synthesizing ethylidenediacetate from methyl acetate or dimethyl ether carbon monoxide and hydrogen in the presence of a catalyst composed of a main component selected from rhodium, palladium, rhodium halides or palladium halides and a co-catalyst selected from organic compounds or inorganic compounds (Example 5 and 8). However, noble metals are expensive [refer to Hydrocarbon Process 54 June 83 (1975)] so if a noble metal is used as the catalyst for carrying out a reaction on an industrial scale, loss of the noble metal catalyst should be prevented. For example, KAKTAF 29 (5) page 376, 1975 discloses a process for preventing a rhodium complex from being reduced to metallic rhodium under a reducing atmosphere. Japanese Patent Publication (laid open) No. 90204/1978 discloses a process for preventing rhodium from evaporating from the reaction system during separation of the product, thereby leaking out of the reaction system. In a process for producing ethylidenediacetate, the equipment for preventing loss of the noble metal catalyst is complicated. This is one of the shortcomings in the synthesis of ethylidenediacetate.

SUMMARY OF THE INVENTION

The present inventors carried out research to find a process for synthesizing ethylidendiacetate using a cheaper catalyst. As a result, we found that a catalyst containing coblat or nickel is effective for such synthesis of ethylidendiacetate.

An object of this invention is to provide a process for synthesizing ethylidenediacetate in the presence of a catalyst containing cobalt or nickel.

This invention relates to a process for producing ethylidenediacetate which comprises reacting methyl acetate or dimethyl ether, carbon monoxide and hydrogen in the presence of a catalyst comprising as a secondary component at least one material selected from the group consisting of iodides and bromides and as a main component at least one material selected from the group consisting of nickel, nickel compounds, cobalt and cobalt compounds under substantially anhydrous conditions.

DETAILED DESCRIPTION OF THE INVENTION

The mechanism of the hydrocarbonylation reaction of methyl acetate or dimethyl ether is not perfectly clear. However, it is believed that the reaction can be expressed in the following equation:

(1) When methyl acetate is used as a raw material $$2CH_3COOCH_3 + 2CO + H_2 \rightarrow CH_3CH(OCOCH_3)_2 + CH_3COOH$$

(2) When dimethyl ether is used as a raw material $$2CH_3OCH_3 + 4CO + H_2 \rightarrow CH_3CH(OCOCH_3)_2 + CH_3COOH$$

In synthesis of ethylidenediacetate according to this invention, a metal or a metal compound selected from nickel, cobalt, nickel compounds or cobalt compounds is used as a main component and a halide selected from the group consisting of iodides, or bromides is used as a secondary component.

The main components include nickel, cobalt, organic or inorganic nickel compounds and organic or inorganic cobalt compounds. Examples of the main catalyst component include nickel powder, nickel compounds, such as nickel acetate, nickel iodide, nickel acetylacetonate, nickel tetracarbonyl, nickel dicarbonyl, nickel dicarbonyl bis-triphenylphosphine, tetramethyl ammonium nickel iodide; cobalt powder and cobalt compounds, such as cobalt hydroxide, cobalt carbonate, cobalt acetylacetonate, cobalt iodide, cobalt acetate, dicobalt octacarbonyl, tetracobalt dodecacarbonyl, cobalt hydride tetracarbonyl, dicobalt hexacarbonyl bis(-tri-n-butylphosphine).

Hereinafter cobalt and/or cobalt compound is referred to for convenience as cobalt component, and similarly, nickel and/or nickel compound is referred to for convenience as nickel component. Cobalt component alone may be used as the component. Nickel component alone may be used as the main component, too. However, a combination of cobalt component and nickel component is particularly effective.

An iodide, a bromide and mixture thereof may be used as a secondary component. The iodide is preferred. When iodine ($I_2$ or $I_3^-$) is added to the reaction system, it is converted to iodides. Similarly, when bromine is added to the reaction system, it is converted to bromides. Therefore, iodine or bromine may be used as a secondary component in place of an iodide or a bromide, or together with an iodide or a bromide. The preferable iodides and iodine which can be used as a secondary component include the following:

(a) $RI_n$           (I)

wherein R is hydrogen or alkyl and n is an integer of 1–3, (b) $I_2$ or $I_3^-$                                                            (II)

(c) $R'COI$                                                           (III)

wherein R' is a alkyl (d) $MI_n$                                                          (IV)

wherein M is alkali or alkaline earth metal, n is 1 or 2 and (e) $R''_4M'I$, $R''_4M'I_3$ or $R''_3M'I_2$            (V)

wherein R" is hydrogen, alkyl or aryl and M' is nitrogen, phosphorus or antimony.

Examples of the secondary component include $I_2$, HI, $KI_3$, $CH_3I$, $C_2H_5I$, $C_3H_7I$, $C_4H_9I$, $CH_2I_2$, $C_2H_4I_2$, $CH_2IBr$, $CHI_3$, $C_2H_4IBr$, $CH_3COI$, $C_2H_5COI$, NaI, KI, LiI, $CaI_2$ and the like.

The hydrocarbonylation reaction of methyl acetate or dimethyl ether of this invention sufficiently proceeds in the presence of the catalyst containing the above mentioned main component and the above mentioned secondary component. An organic promoter or an inorganic promoter may be used with the catalyst in order to increase the reaction rate. An organic promoter is preferable. The more effective organic promoter is a non-hydrocarbon material that can form a coordination compound with the nickel and/or cobalt component and has one or more electron pairs being capable of forming a coordination bond with the metal component in the catalyst. The organic promoter may be introduced into the reaction system with the reactants.

Examples of preferable promoters are the compounds represented by the formula

wherein M" is N, P, Sb or As and $R^1$, $R^2$ and $R^3$ may be the same or different, and independently hydrogen, or alkyl having 1-10 carbon atoms, cycloalkyl having 3-10 carbon atoms or aryl having 7-10 carbon atoms. Examples of the promoters include amines, such as monomethyl amine, dimethyl amine, trimethyl amine, dimethyl ethyl amine, diethyl amine, tri-iso-propyl amine, tri-n-propyl amine, tri-n-butylamine, tri-tert.-butylamine, aniline, dimethyl aniline, diethyl aniline and the like; phosphines, such as tri-n-tropyl phosphine, tri-isopropyl phosphine, tri-n-butyl phosphine, tri-tert.-butyl phosphine, tricyclohexyl phosphine, ethylene bis(diphenyl phosphine), triphenyl phosphine and the like; arsines, such as trimethyl arsine, triethyl arsine, tri-isopropyl arsine, tripropyl arsine, tricyclohexyl arsine, phenyl di-iso-propyl arsine, diphenyl arsine, bis(diphenyl arsino)ethane, bis(di-iso-propyl arsino)hexane, and the like; and stibines, such as tri-iso-propyl stibine, ethyl-di-iso-propyl stibine, triphenyl stibine, tri(o-tolyl)stibine, phenyl diamyl stibine, tris(diethyl aminomethyl)stibine, bis(diethylstibino)pentane and the like.

In addition to the above listed compounds, organic nitrogen compounds and organic compounds having oxygen or phosphorus atom and nitrogen atom may be used as promoter for the reaction.

Examples of the organic nitrogen compounds include heterocyclic compounds such as pyrrole, pyrrolidine, piperidine, pyrimidine, picolines, pyrazine and N-alkyl ($C_1$-$C_5$) substituted derivatives of the above mentioned compounds such as N-methylpyrrolidine, benztriazole, piperazine, N-methyl piperazine, N-ethyl piperazine, 2-methyl-N-methylpiperazine. 2,2-dipyridyl, methyl-substituted 2,2-dipyridyl, 1,4-diazabicyclo(2,2,2)octane, methyl-substituted 1,4-diazabicyclo(2,2,2)octane, purine, 2-aminopyridine, 1,10-phenanthroline, methyl-substituted 1,10-phenanthroline, 2-(dimethylamine)pyridine, 2-(dimethylamino)-6-methoxyquinoline, 7-chloro-1,10-phenathroline, 4-triethylsilyl-2,2'-dipyridyl, 5-(thiabenzyl)-1,10-phenanthroline, pyridine, 2,4-dimethyl pyridine, 2,6-dimethyl pyridine, 2,4,6-trimethylpyridine, imidazole and the like; diamines, such as N,N,N',N'-tetramethyl ethylene diamine, N,N,N',N'-tetraethyl ethylene diamine, N,N,N',N'-tetra-n-propyl ethylene diamine, N,N,N',N'-tetramethyl methylene diamine, N,N,N',N'-tetraethyl ethylene diamine, N,N,N',N'-tetra-iso-butyl methylene diamine, and the like; and nitriles, such as acetonitrile, propionitrile, adiponitrile, benzonitrile and the like.

The organic compounds having oxygen or phosphorus atom and nitrogen atom include hydroxy or carbonyl-substituted above mentioned organic nitrogen compound, such as 2-hydroxypyridine, methyl-substituted 2-hydroxypyridine, picolinic acid, methyl-substituted picolinic acid, 2,5-dicarboxy piperazine, ethylenediamine tetraacetic acid, 2,6-dicarboxy pyridine, 8-hydroxy quinoline, 2-carboxyquinoline, cyclohexane-1,2-diamine-N,N,N',N'-tetraacetic acid, salts of ethylenediamine tetraacetic acid, such as tetramethyl ester of ethylenediamine tetraacetic acid, ammonium salts like ammonium acetate; carboxylic amides, such as acetamide, acetanilide, N,N-dimethyl acetamide, N-methyl-N-phenyl acetamide and the like; amino acid, such as N,N-dimethyl glycine, N,N-diethyl glycine and the like; 1-methyl-2-pyrrolidinone, 4-methyl morpholine N,N,N',N'-tetramethyl urea, N-methyl iminodiacetic acid, nitrilotriacetic acid, N-methyl iminodiacetic acid, phosphine, iminium salts such as triphenyl phosphine iminium chloride. Of these promoters, organic promoters having trivalent phosphorus and trivalent nitrogen are preferred.

Effective inorganic promoters include metals having atomic weight of at least 6 and belonging to Groups Ia, IIa, IIIa, IVa, Ib, IIb, Vb, VIb and VIIb of the Periodic Table compounds of these metals. Metals having atomic weight of less than 120 and compounds of the metals are preferable as inorganic promoters. Lithium, sodium, potassium, magnesium, calcium, aluminum, tin, zinc, cadmium, copper, manganese, chromium, vanadium and compounds of the metals are preferred.

Elemental metals are usable in the form of finely milled powder. Organic or inorganic compounds of the metals are usable.

Particularly, oxides, hydroxides, halides, such as bromides, and iodides, oxyhalides, hydrides, carbonyls, alkoxides, nitrates, nitrites, phosphates, and phosphites of the metal and aliphatic, alicyclic, naphthenic and monocarboxylates of the metals, such as acetates, butyrates, decanoates, laurylates, stearates, and benzoates of the metals are typical inorganic promoters. Metal chelates, associate compounds of the metals and enol salts of the metals are also preferable as promoter. Particularly preferable inorganic promoters include bromides, iodides and organic acid salts, such as acetates of the metals. The use of both an organic promoter and an inorganic promoter with the metal component as main component is preferred.

The amount of cobalt component and/or nickel component employed as the main component may be in the range of from $10^{-6}$ to 5 mol, preferable $10^{-4}$–4 mol, more preferably $10^{-3}$ to 2 mol, and most preferably $5\times10^{-3}$ to 1.0 mol per liter of total amount of starting material and solvent. The amount of iodide component and/or bromide component employed as secondary component may be in the range of from $10^{-6}$ to 20 equivalent weight, preferably $10^{-4}$ to 10 equivalent weight per liter of total amount of starting material and solvent.

The amount of the organic or inorganic promoter employed depends on the amount of main catalyst employed. In general, the amount of the organic or inorganic promoter employed may be in the range of from $10^{-6}$ to 10 mol, preferably $10^{-4}$ to 5 mol per liter of total amount of starting material and solvent.

In practicing this invention, the reaction temperature is not critical. In general, the reaction temperature may be in the range of 20° C.–500° C., preferably 80°–350° C., more preferably 100°–300° C.

The reaction pressure is kept high enough to keep methyl acetate or dimethyl ether, the solvent and the product in a liquid phase and to maintain an appropriate partial pressure of each of carbon monoxide and hydrogen. The partial pressure of each of carbon monoxide and hydrogen may be in the range of 0.5–700 atm, preferably 1–600 atm, and more preferably 3–500 atm. However, the partial pressure of each of carbon monoxide and hydrogen may be in the range of 0.05–1000 atm.

Stoichimetric amounts of the raw material gas depend on which one of methyl acetate, dimethyl ether and mixture thereof is used. Therefore, stoichimetric amounts of carbon monoxide and hydrogen may very from molar ratio of CO to $H_2$ of 2:1 to molar ratio of CO to $H_2$ of 4:1. It is not necessarily critical to use CO and $H_2$ in stoichiometric amounts. In general, the molar ratio of CO to $H_2$ may be in the range of from 1:100 to 100:1, preferably 1:50 to 50:1 and more preferably 1:10 to 10:1. However, it is preferable that carbon monoxide and hydrogen be used in an approximately stoichimetric amount. So, preferably, the ratio of carbon monoxide to hydrogen may be in the range of 0.5:1 to 5:1.

In the practice of this invention, carbon monoxide and hydrogen may be introduced into the reaction system as separate streams. Synthesis gas comprising carbon monoxide and hydrogen may be introduced into the reaction system. The raw material gas composed of carbon monoxide and hydrogen does not need to be highly pure and may contain carbon dioxide, methane, nitrogen, and rare gases. Low concentration of each of carbon monoxide and hydrogen in the mixed gas is not preferable, because the reaction pressure must rise in case of using such gas.

In the present process, methyl acetate or dimethyl ether as a raw material and ethylidenediacetate as a product serve as a solvent for reaction, so another solvent is not necessary. An organic solvent and a diluent compatible with the raw materials and the product under the reaction conditions may be used. Examples of the organic solvent include organic acids, such as acetic acid, propionic acid, butyric acid, octanoic acid, phthalic acid, benzoic acid; esters of organic acids, such as methyl acetate, ethyl acetate, ethylene glycol diacetate, propylene glycol diacetate, dimethyl adipate, methyl benzoate, ethyl benzoate, dimethyl phthalate, diethyl phthalate, dioctyl phthalate, phenyl acetate, and tolyl acetate; hydrocarbons, such as dodecane, hexadecane, benzene, naphthalene, and biphenyl; esters of inorganic acids, such as triphenyl phosphate, tricresyl phosphate, dibutylphenyl phosphate, silicates such as tetramethyl ortho-silicate, and tetrabutyl silicate; ketones, such as aromatic ethers, such as diphenyl ethers; ketones, such as acetone, methyl ethyl ketone, dibutyl ketone, methyl isobutyl ketone, acetophenone, and benzophenone.

The product, ethylidenediacetate, produced according to this invention is likely to decompose in the presence of water. After the raw material and the solvent have been dried to a substantially anhydrous state, they should be introduced into the reaction system. The reaction system should be kept in a substantially anhydrous state. In other words, water content in the reaction system should be kept to less than 10 mol % on the basis of total mol of the liquid components present in the reaction system, preferably less than 5 mol % and more preferably less than 3 mol %.

The present process may be carried out by a batch, semicontinuous or continuous method. In a continuous method the raw material and the catalyst are continuously introduced into the reaction system; and the product is continuously distilled to separate it from the reaction system and the catalyst is recirculated into the reaction system for reuse. Alternatively, the reaction mixture containing ethylidenediacetate which is withdrawn from the reaction system may be introduced into another reactor, where ethylidenediacetate contained in the mixture is converted to vinyl acetate and acetic acid. The reaction mixture is distilled to separate methyl acetate, acetic acid and vinyl acetate from the mixture and to recover them separately. The catalytic composite-containing residue is recirculated into the reaction system.

According to this invention, ethylidenediacetate is produced by using a less expensive catalyst in a hydrocarbonylation reaction.

The present invention is further illustrated by the non-limiting following Examples.

EXAMPLE 1

Into an autoclave were charged 1.50 grs of $Co_2(CO)_8$, 35.5 grs of $CH_3I$, 11.7 grs of tri-n-butylamine, $(n-C_4H_9)_3N$ 48 grs of acetic acid (solvent) and 59.2 grs of methyl acetate as a raw material. Hydrogen (100 Kg/cm$^2$) and carbon monoxide (100 Kg/cm$^2$) under pressure were charged into the autoclave.

The temperature in the autoclave was raised to 200° C., and the reaction was continued until the absorption of gas could not be detected.

After cooling the reaction mixture, GC-MASS analysis showed that acetaldehyde and ethylidenediacetate were present in the mixture.

EXAMPLE 2

Into an autoclave were charged 0.587 grs of nickel powder, 0.67 grs of LiI, 14.5 grs of $CH_3I$, 4.5 grs of tri-n-butylphosphine $(n-C_4H_9)_3P$, 16 grs of acetic acid as a solvent and 19.8 grs of methyl acetate as a raw material. Hydrogen (100 Kg/cm$^2$) and carbon monoxide (100 Kg/cm$^2$) under pressure were charged into the autoclave at room temperature. The temperature in the autoclave was raised to 200° C. The reaction was carried out at the temperature, until absorption of gas could not be detected.

After cooling the reaction mixture, gas chromatographic (hereinunder referred to as GC) analysis showed that ethylidenediacetate existed in the mixture together with 18 mol % of acetic anhydride.

EXAMPLE 3

Into an autoclave were charged 0.58 grs of nickel powder, 1.00 gr of $Co_2(CO)_8$, 13.4 grs of $CH_3I$, 4.5 grs of tri-n-butylphosphine $(n—C_4H_9)_3P$, 16 grs of acetic acid as a solvent and 19.8 grs of methyl acetate as a raw material. Hydrogen (50 $Kg/cm^2$) and carbon monoxide (100 $Kg/cm^2$) under pressure were charged into the autoclave at room temperature. The temperature in the autoclave was raised to 170° C. The reaction was carried out for 7 hours at this temperature.

After cooling the reaction mixture, GC analysis showed that 37.5 mol % of ethylidenediacetate and 27.4 mol % of acetic anhydride on the basis of the theoretical amount had been formed together with acetic acid.

EXAMPLES 4–14

The procedures were repeated using the raw materials, the catalysts and the solvents as given in Table 1 under the reaction conditions as given in Table 1. The results are shown in Table 1.

TABLE 1

| Example No. | | | 3 | 4 | 5 | 6 |
|---|---|---|---|---|---|---|
| raw material | | | methyl acetate | methyl acetate | methyl acetate | methyl ether |
| amount (g) | | | 19.8 | 19.8 | 19.8 | 19.7 |
| solvent | | | acetic acid | acetic acid | acetic acid | acetic acid |
| amount (g) | | | 16 | 16 | 16 | 16 |
| catalyst | nickel compound | | Ni powder | Ni powder | Ni powder | Ni powder |
| | amount g | | 0.587 | | 0.435 | 0.193 |
| | cobalt compound | | $Co_2(CO)_8$ | $Co_2(CO)_8$ | $Co_2(CO)_8$ | $Co_2(CO)_8$ |
| | amount g | | 1.00 | 0.333 | 0.40 | 0.3333 |
| | halogen compound | | $CH_3I$ | $CH_3I$ | $CH_3I$ | $CH_3I$ |
| | amount g | | 13.4 | 13.4 | 13.4 | 13.6 |
| promoter | organic promoter | | $(n-C_4H_9)_3P$ | $(n-C_4H_9)_3P$ | $(n-C_4H_9)_3P$ | $(n-C_4H_9)_3P$ |
| | amount g | | 4.5 | | 3.3 | 3.9 |
| | inorganic promoter | | — | — | — | — |
| | amount g | | | | | |
| reaction conditions | temp. °C. | | 170 | 175 | 175 | 200 |
| | pres. $Kg/cm^2$ | total pres. | 180 | 180 | 180 | 160 |
| | | CO partial pres. | 120 | 120 | 90 | 80 |
| | | $H_2$ partial pres. | 60 | 60 | 90 | 80 |
| | time hrs | | 7 | 5 | 5 | 3 |
| product | ethylidene diacetate % | | 37.5 | 20.3 | 12.8 | 7.2 |
| | acetic anhydride % | | 27.4 | 44.7 | 39.4 | 32.7 |

| Example No. | | | 7 | 8 | 9 | 10 |
|---|---|---|---|---|---|---|
| raw material | | | methyl acetate | methyl acetate | methyl acetate | dimethyl ether |
| amount (g) | | | 19.8 | 19.8 | 19.8 | 12.3 |
| solvent | | | acetic acid | acetic acid | acetone | acetic acid |
| amount (g) | | | 16 | 16 | 18 | 16 |
| catalyst | nickel compound | | $NiI_2$ | Ni powder | $NiI_2$ | Ni powder |
| | amount g | | 1.04 | 0.294 | 1.04 | 0.435 |
| | cobalt compound | | $Co_2(CO)_8$ | $Co_2(CO)_8$ | $Co_2(CO)_8$ | $Co_2(CO)_8$ |
| | amount g | | 0.333 | 1.72 | 0.333 | |
| | halogen compound | | $CH_3I$ | $CH_3I$ | $CaI_2$ | $CH_3I$ |
| | amount g | | 12.0 | 13.6 | 12.4 | 13.4 |
| promoter | organic promoter | | 2,6-lutidine | $(n-C_4H_9)_3N$ | | $(n-C_4H_9)_3P$ |
| | amount g | | 1.14 | 4.08 | 1.45 | 4.5 |
| | inorganic promoter | | — | Al powder | — | — |
| | amount g | | | 0.24 | | |
| reaction conditions | temp. °C. | | 210 | 180 | 200 | 185 |
| | pres. $Kg/cm^2$ | total pres. | 160 | 160 | 180 | 200 |
| | | CO partial pres. | 80 | 80 | 120 | 150 |
| | | $H_2$ partial pres. | 80 | 80 | 60 | 50 |
| | time hrs | | 4 | 8 | 7 | 6 |
| product | ethylidene diacetate % | | 2.6 | 6.3 | 1.0 | 16.7 |
| | acetic anhydride % | | 31.3 | 33.4 | | 35.3 |

| Example No. | | 11 | 12 | 13 | 14 |
|---|---|---|---|---|---|
| raw material | | methyl acetate | methyl acetate | methyl acetate | methyl ether |
| amount (g) | | 59.4 | 59.2 | 59.2 | 19.8 |
| solvent | | acetic anhydride | acetic acid | acetic acid | ethylene diglycol diacetate |
| amount (g) | | 54 | 48 | 48 | 16 |
| catalyst | nickel compound | Ni powder | Ni powder | Ni powder | $Ni[P(C_6H_5)_3]_2(CO)_2$ |
| | amount g | 0.200 | 0.587 | 0.587 | 6.39 |
| | cobalt compound | $Co_2(CO)_8$ | $Co_2(CO)_8$ | $Co_2(CO)_8$ | $Co_2(CO)_8$ |
| | amount g | 4.66 | 1.3 | 1.3 | 0.333 |
| | halogen compound | $CH_3I$ | $CH_3I$ | $CH_3I$ | $CH_3I$ |
| | amount g | 35.5 | 35.5 | 35.5 | 13.4 |
| promoter | organic promoter | $(n-C_4H_9)_3P$ | $(C_6H_5)_3P$ | $(n-C_4H_9)_3P$ | |
| | amount g | 1.38 | 13.85 | 4.5 | |
| | inorganic promoter | Al powder | $Cr(CO)_6$ | | $SnI_4$ |
| | amount g | 0.32 | 2.2 | | 3.13 |

TABLE 1-continued

| reaction conditions | temp. °C. | | 170 | 180 | 200 | 185 |
|---|---|---|---|---|---|---|
| | pres. Kg/cm² | total pres. | 140 | 120 | 150 | 180 |
| | | CO partial pres. | 70 | 60 | 100 | 120 |
| | | H₂ partial pres. | 70 | 60 | 50 | 60 |
| | time hrs | | 10 | 7 | 3 | 7 |
| product | ethylidene diacetate % | | 28.8 | 9.2 | 15.7 | 8.2 |
| | acetic anhydride % | | 2.8 | 21.7 | 0.9 | 29.5 |

EXAMPLE 15

Into an autoclave were charged 0.587 grs of nickel powder, 1.00 gr of $Co_2(CO)_8$, 35.5 grs of $CH_3I$, 4.5 grs of tri-n-butylphosphine, $(n-C_4H_9)_3P$ 48 grs of acetic acid as a solvent and 59.2 grs of methyl acetate as a raw material. A mixed gas of hydrogen and carbon monoxide under pressure was charged in the autoclave at total pressure of 80 Kg/cm² (partial pressure of hydrogen: 26.7 Kg/cm² and partial pressure of carbon monoxide: 53.3 Kg/cm²) at room temperature.

The temperature in the autoclave was raised to 175° C., and the reaction was carried out for 8 hours while the pressure in the autoclave was kept constant by introducing thereinto a mixed gas of 1 mol of hydrogen and 2 mol of carbon monoxide.

After cooling the reaction mixture, GC analysis showed that 25.4 mol % of ethylidenediacetate and 20.0 mol % of acetic anhydride on the basis of theoretical amount had been formed together with acetic acid.

EXAMPLE 16

Into an autoclave were charged 3.2 grs of nickel dicarbonyl-bis(triphenyl phosphine), $Ni[P(C_6H_5)_3]_2(CO)_2$, 1.0 gr of $Co_2(CO)_8$, 13.4 grs of $CH_3I$, 16 grs of acetic acid as a solvent and 19.8 grs of methyl acetate as a raw material. Hydrogen (60 Kg/cm²) and carbon monoxide (100 Kg/cm²) under pressure were charged into the autoclave at room temperature.

The temperature in the autoclave was raised to 175° C., and the reaction was carried out for 10 hours at this temperature. After cooling the reaction mixture, GC analysis showed that 8.2 mol % of ethylidenediacetate and 31.5 mol % of acetic anhydride on the basis of theoretical amount were formed together with acetic acid.

EXAMPLE 17

Into an autoclave were charged 1.8 grs of bis(tri-n-butylamine)cobalt diiodide, namely $CoI_2[(n-C_4H_9)_3N]_2$ 3.5 grs of $CH_3I$ and methyl acetate as a raw material. Synthesis gas containing 10 mol % of hydrogen under pressure was chareged into the autoclave at 450 Kg/cm².

The temperature in the autoclave was raised to 175° C., and the reaction was effected at this temperature, until absorption of gas could not be detected. The temperature of the reaction mixture was raised at 190° C. and then it was cooled.

GC analysis showed that 0.7 grs of ethylidenediacetate has been formed together with acetic acid. This amount is 3.8 mol % on the basis of theoretical amount.

EXAMPLE 18

Into an autoclave were charged 18.4 grs of cobalt iodide, 0.33 grs of cobalt octacarbonyl, 24.0 grs of N,N-dimethylacetamide (solvent) and 16 grs of methyl acetate (raw material). Hydrogen (50 Kg/cm²) and carbon monoxide (190 Kg/cm²) under pressure were charged in the autoclave at room temperature. The temperature in the autoclave was raised to 210° C., and the reaction was continued until the absorption of gas could not be detected. After cooling the reaction mixture, GC-MASS analysis showed that 3.7 mol % of acetic anhydride and ethylidenediacetate were present therein.

EXAMPLE 19

Into an autoclave 3.1 grs of basic cobalt carbonate and 30 grs of phenyl acetate. Hydrogen (50 Kg/cm²) and carbon monoxide (140 Kg/cm²) under pressure were charged into the autoclave at room temperature.

The temperature in the autoclave was raised to 150° C., and the reaction was carried out for 2 hours at that temperature. After allowing the reaction mixture to stand for cooling, the pressure in the autoclave was depressured to 30 Kg/cm². Into the autoclave were charged 2.7 grs of 2.4-lutidine, 10 grs of methyl iodide and 16 grs of methyl acetate under pressure were charged into the autoclave. The pressure in the autoclave was raised to 190 Kg/cm² by introducing a synthesis gas ($CO:H_2=3:1$ by volume) thereinto.

The temperature in the autoclave was raised to 230° C., and the reaction was continuted at that temperature under absorption of gas could not be detected. After cooling the reaction mixture, GC-MASS analysis showed ethylidenediacetate was present.

EXAMPLE 20

Into an autoclave were charged 0.417 grs of nickel powder, 2.64 grs of lithium acetate, 1.52 grs of 2.4-lutidine, 24 grs of acetic acid (solvent) and 29.6 grs of methyl acetate (raw material). Air in the reactor was purged with carbon monoxide, and then the temperature in the autoclave was raised to 200° C. with stirring. Hydrogen (10 Kg/cm²) and carbon monoxide (55 Kg/cm²) under pressure were charged into the autoclave until the pressure in the autoclave was raised to 80 Kg/cm². The reaction was continued for 2 hours while maintaining that pressure.

After cooling the reaction mixture, GC analysis showed that 37.8 mol % of acetic anhydride and 2.0 mol % of ethylidenediacetate were present therein.

What is claimed is:

1. A process for producing ethylidenediacetate which comprises reacting methyl acetate or dimethyl ether, carbon monoxide and hydrogen in the presence or absence of a solvent and in the presence of a catalyst consisting essentially of (a) as a main catalyst component, a combination of (1) at least one metal material selected from the group consisting of nickel and nickel compounds and (2) at least one metal material selected from the group consisting of cobalt and cobalt compounds, and (b) as a secondary catalyst component, at least one material selected from the group consisting of iodides having the formula $RI_n$ wherein R is an alkyl radical having 1 to 4 carbon atoms and n is an integer of 1 to 3, under substantially anhydrous conditions, the amount of each of the metal materials (1) and (2) being in the range of from $5 \times 10^{-3}$ to 1.0 mol per liter of the total amount of the starting material and solvent if present, and the amount of the secondary catalyst component being in the range of $10^{-4}$ to 10 equivalent weight per liter of the total amount of the starting material and solvent if present.

2. The process of claim 1 wherein said metal material (1) is selected from the group consisting of nickel powder, nickel acetate, nickel iodide, nickel acetylacetonate, nickel tetracarbonyl, nickel dicarbonyl, nickel dicarbonyl bistriphenylphosphine, tetramethyl ammonium nickel iodide, and mixtures thereof.

3. The process of claim 1 wherein said metal material (2) is selected from the group consisting of cobalt powder, cobalt hydroxide, cobalt carbonate, cobalt acetylacetate, cobalt iodide, cobalt acetate, dicobalt octacarbonyl, tetracobalt dodecacarbonyl, cobalt hydride tetracarbonyl, dicobalt hexacarbonyl bis(tri-n-butylphosphine) and mixtures thereof.

4. The process of claim 1 wherein said reaction is carried out in the presence of a solvent, said solvent being at least one solvent selected from the group consisting of organic acids, esters of organic acids, hydrocarbons, esters of inorganic acids, aromatic ethers and ketones.

5. The process of claim 1 wherein said reaction is carried out in the presence of said catalyst, together with at least one organic promoter, said promoter being at least one compound selected from the group consisting of (A) compounds represented by the formula:

wherein M" is a nitrogen group atom selected from the group consisting of N, P, Sb and As, and $R^1$, $R^2$ and $R^3$ are the same or different, and independently hydrogen or a radical selected from the group consisting of an alkyl radical having 1 to 10 carbon atoms, a cycloalkyl radical having 3 to 10 carbon atoms and an aryl radical having 7 to 10 carbon atoms, and (B) heterocyclic nitrogen compounds.

6. The process of claim 1 wherein the partial pressure of each of carbon monoxide and hydrogen is in the range of from 3 to 500 atm.

7. The process of claim 1 wherein said reaction is carried out at a temperature in the range of from 80° C. to 350° C.

8. The process of claim 1 wherein said reaction is carried out in the presence of said catalyst, together with at least one inorganic promoter selected from the group consisting of lithium, sodium, potassium, magnesium, calcium, aluminum, tin, zinc, cadmium, copper, manganese, chromium, vanadium, and compounds of these metals.

9. The process of claim 5 or 8 wherein the amount of said promoter is in the range of from $10^{-4}$ to 5 mol per liter of the total amount of (i) starting material and (ii) solvent if present.

10. The process of claim 1 wherein said secondary component is methyl iodide.

11. The process of claim 4 wherein said solvent is at least one solvent selected from the group consisting of organic acids and esters of organic acids.

12. The process of claim 1 wherein said reaction is carried out in the presence of a solvent selected from the group consisting of acetic acid and acetic anhydride.

13. The process of claim 1, wherein said reaction is carried out at a temperature in the range of from 100° C. to 300° C.

14. The process of claim 1 wherein the molar ratio of carbon monoxide to hydrogen is in the range of from 1:100 to 100:1.

15. The process of claim 1 wherein the molar ratio of carbon monoxide to hydrogen is in the range of from 1:10 to 10:1.

16. The process of claim 1 wherein the molar ratio of carbon monoxide to hydrogen is in the range of from 0.5:1 to 5:1.

17. The process of claim 5 wherein said organic promoter is at least one compound selected from the group consisting of monomethyl amine, dimethyl amine, trimethyl amine, dimethyl ethyl amine, diethyl amine, tri-iso-propyl amine, tri-n-propyl amine, tri-n-butylamine, tri-tert.-butylamine, aniline, dimethyl aniline, diethyl aniline, tri-n-propyl phosphine, tri-iso-propyl phosphine, tri-n-butyl phosphine, tri-tert.-butyl phosphine, tricyclohexyl phosphine, ethylene bis(diphenyl phosphine), triphenyl phosphine, trimethyl arsine, triethyl arsine, tri-iso-propyl arsine, tripropyl arsine, tricyclohexyl arsine, phenyl di-iso-propyl arsine, diphenyl arsine, bis(diphenyl arsino)ethane and bis(di-iso-propyl arsino)hexane, tri-iso-propyl stibine, ethyl-di-iso-propyl stibine, triphenyl stibine, tri(o-tolyl)stibine, phenyl diamyl stibine, tris(diethylaminomethyl)stibine and bis(diethylstibino)pentane.

18. The process of claim 5 wherein said organic promoter is tri-n-butylphosphine.

* * * * *